United States Patent [19]
Pastyr et al.

[11] Patent Number: 6,045,558
[45] Date of Patent: Apr. 4, 2000

[54] WHOLE BODY STEREOTAXIC DEVICE

[75] Inventors: Otto Pastyr, Laiman; Wolfgang Schlegel, Heidelberg, both of Germany

[73] Assignee: Deutsches Krebsforschungszentrum Stiftung des Offentlichen Rechts, Heidelberg, Germany

[21] Appl. No.: 09/011,795

[22] PCT Filed: Aug. 14, 1996

[86] PCT No.: PCT/DE96/01521

§ 371 Date: Aug. 19, 1998

§ 102(e) Date: Aug. 19, 1998

[87] PCT Pub. No.: WO97/00067

PCT Pub. Date: Feb. 27, 1997

[30] Foreign Application Priority Data

Aug. 14, 1995 [DE] Germany .................. 195 29 867

[51] Int. Cl.[7] .................................................. A61B 6/04
[52] U.S. Cl. .................................................. 606/130
[58] Field of Search ................... 606/1, 130; 378/180; 5/425, 428, 625

[56] References Cited

U.S. PATENT DOCUMENTS 3,859,982  1/1975  Dove .
4,262,204  4/1981  Mirabella .
5,242,455  9/1993  Skeens et al. .
5,281,232  1/1994  Hamilton et al. .
5,665,095  9/1997  Jacobson .................. 606/130
5,681,326  10/1997  Lax ......................... 606/130

FOREIGN PATENT DOCUMENTS

WO90/00372  1/1990  WIPO .

Primary Examiner—Michael Buiz
Assistant Examiner—William Lewis
Attorney, Agent, or Firm—Steven J. Hultquist; William A. Barrett; Edward H. Green, III

[57] ABSTRACT

A whole body stereotaxis apparatus comprising a base plate (2) to accommodate a patient, two side strips (4, 6) which are attached to the base plate (2) at the marginal or side edges thereof and laterally delimit the base plate (2) and to which arches (10, 12) extending over the base plate (2) can be attached, characterized in that a central strip (8) is mounted on the base plate (2) and comprises bores (22) to accommodate accessories.

17 Claims, 3 Drawing Sheets

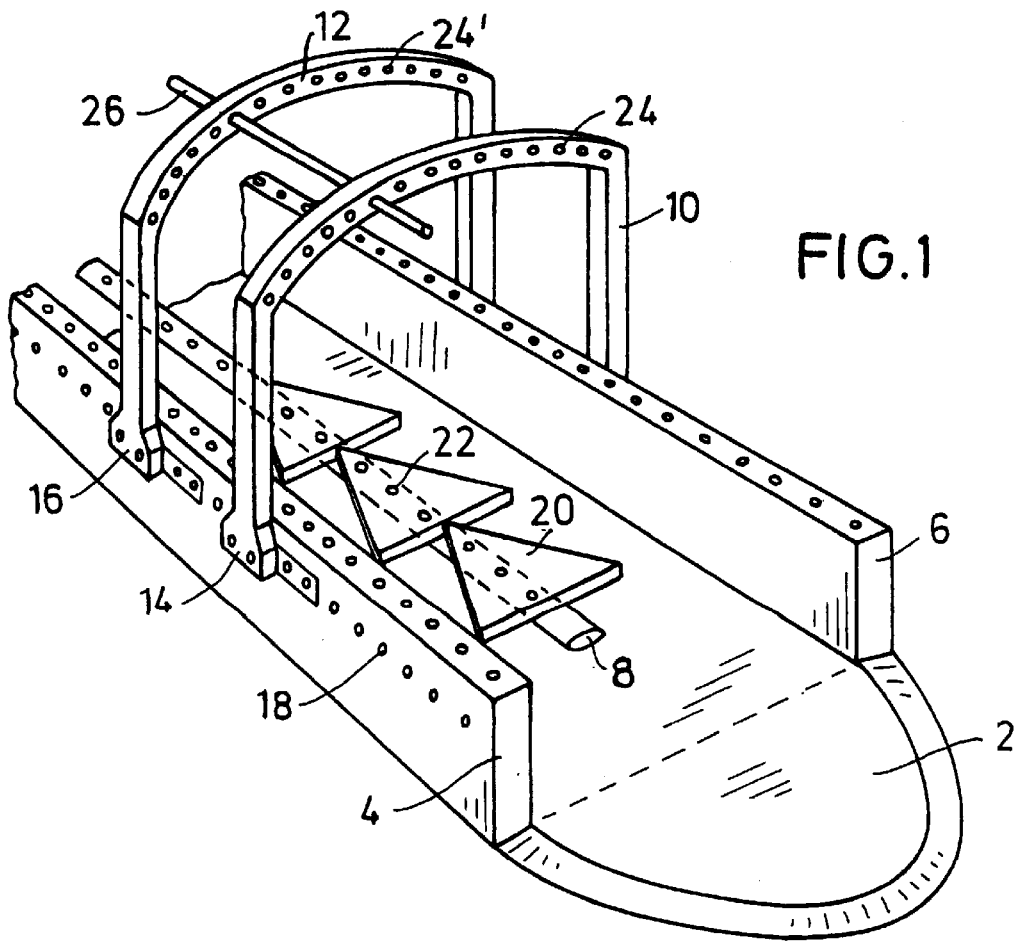
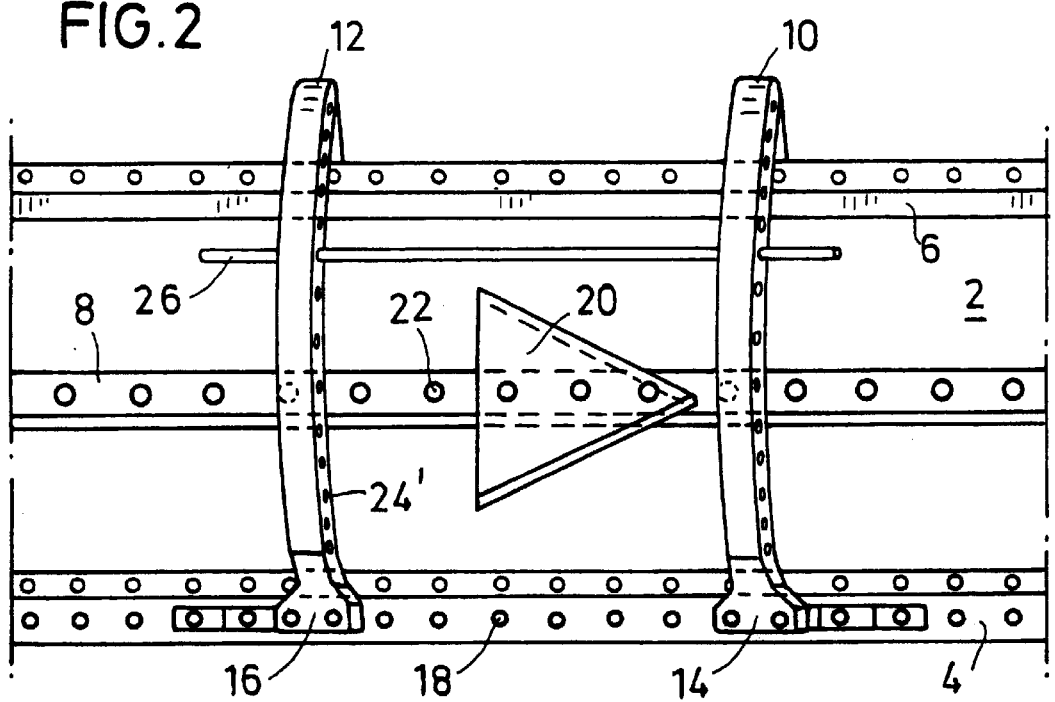

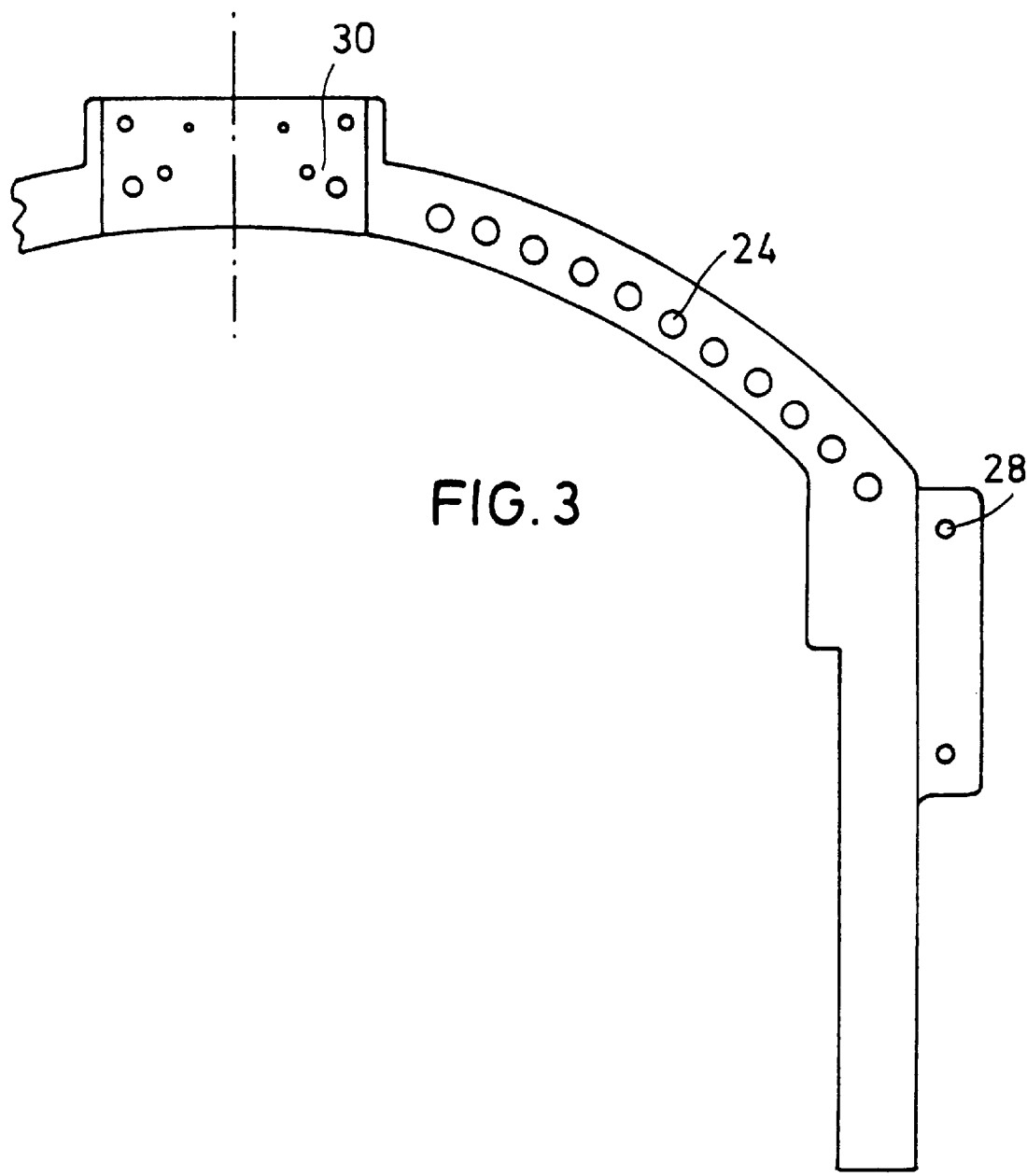
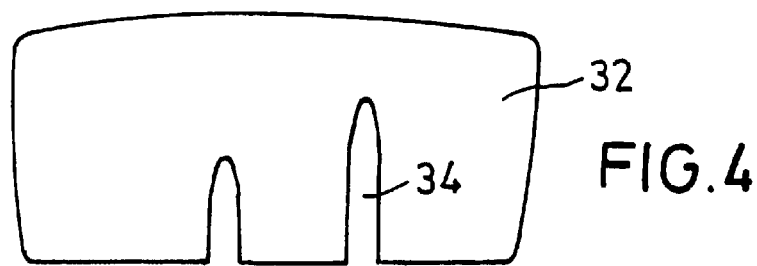

WHOLE BODY STEREOTAXIC DEVICE

BACKGROUND OF THE INVENTION

FIELD OF THE INVENTION

The previously known whole body stereotaxis apparatus has a base plate and two curved marginal or side strips which border thereon and are attached thereto at the marginal or side edges thereof. The two side strips are connected by hoops or arches extending over the base plate. This whole body stereotaxis apparatus is disadvantageous, since it is lacking the possibility of accurately localizing points in the area of the base plate center. By this, a patient's body resting upon the base plate can also be localized only inaccurately in the area bordering on the base plate. Furthermore, the rod-like calibration rods of said publication are awkward and only permit a calibration of the arch to which they are fixed. In addition, the arrangement of this publication is lacking means for target-positioning the entire apparatus for a subsequent irradiation of the patient. Finally, two adjacent arches are not defined accurately with respect to each other as regards their relative positioning.

It is the object of the present invention to provide a whole body stereotaxis apparatus which avoids the drawbacks of said prior art and particularly permits an accurate localization also in the area of the base plate and areas bordering thereon. In this connection, calibration means which can easily be manipulated shall be provided, and the relative positioning of adjacent arches shall be facilitated.

According to one aspect of the present invention a whole body stereotaxis apparatus according to the preamble of claim 1 shall be provided, which is characterized in that a central strip having bores for receiving accessories is secured to the base plate. The central strip can accommodate particular calibration means which thus also permit a calibration in the area of the base plate.

According to a further aspect of the present invention, a whole body stereotaxis apparatus is provided which is characterized in that two opposite arches are fixed to the side strips, and the arches are connected by at least one holding bar which serves for holding surgical instruments. The holding bar defines a clear distance between the two adjacent arches so as to facilitate the localization of surgical instruments mounted on the holding bar. The distance between the two arches does not change even while the surgical instruments fixed to the holding bar are actuated.

According to a third aspect of the present invention a whole body stereotaxis apparatus according to claim 3 is provided, which is characterized in that at least one arch is fixed to the side strip and the arch carries target setting means for the subsequent irradiation of the patient. The target setting means enable accurate positioning of the entire whole body stereotaxis apparatus with respect to an irradiation system.

The base plate preferably contains carbon fibers. They contribute considerably to the stability of the base plate.

The base plate preferably contains acrylic foam. It increases the flexibility of the carbon fibers.

In an especially preferred embodiment, the base plate alternately comprises a layer of acrylic foam and a layer of plastics fibers sandwiched together. By this it is possible to achieve especially satisfactory results as regards lightness or low weight, manipulability and flexibility of the base plate.

It is preferred to secure calibration means to one arch or to the central strip, which supplies a defined reference point in computer tomography. The calibration means preferably has a localization plate triangular in cross-section and accommodating metal wires. The metal wires supply a reference point or a reference line in computer tomography by means of which the stereotaxis apparatus can be calibrated.

It is preferred to equip the base plate with immobilizing means for the patient, particularly a vacuum mattress. It serves for the clear and position-stable fixation or immobilization of the patient with respect to the stereotaxis apparatus. The vacuum mattress is wrapped around the patient and then evacuated to stiffen it.

It is preferred to provide holding metal sheets which are inserted between side strip and immobilizing means to facilitate the patient's immobilization.

For an accurate positioning it is preferred to fix a localization plate to the arch and a localization plate to the central strip, the two localization plates being in vertical alignment with each other. By this it is possible to accurately position the whole body stereotaxis apparatus.

A surgical instrument serving the immobilization of the spinal column is attached to the holding bar. As regards its position the holding bar is defined accurately relative to the two arches and enables a clear and position-stable fixation of a surgical instrument serving for immobilizing the spinal column of the patient, so that the patient is positioned clearly and immovably with respect to the stereotaxis apparatus.

It is especially preferred to divide the arch into two parts so as to optionally disassemble one side thereof. This increases the spectrum of its possible uses.

Three target setting means are preferably fixed to the arch. This permits an effective positioning of the two marginal areas and the central area of the whole body stereotaxis apparatus.

It is especially preferred to secure to the arch an auxiliary arch which offers further possibilities of medical treatment or diagnosis, particularly for a biopsy. A slide which is slidably supported is preferably fixed to the auxiliary arch. Such a slide enables rapid target setting along the path of the auxiliary arch. Further advantages, features and possible uses of the invention follow from the below description of various embodiments in connection with the drawing.

BRIEF DESCRIPTION OF THE FIGURES

FIG. 1 is a perspective view of a whole body stereotaxis apparatus according to the invention.

FIG. 2 is a side view of the embodiment of FIG. 1 in perspective.

FIG. 3 is a view of the two-part arch of the invention.

FIG. 4 is a top view onto the holding metal sheets employed in the present invention.

DESCRIPTION OF THE PREFERRED EMBODIMENTS

Figure 5:
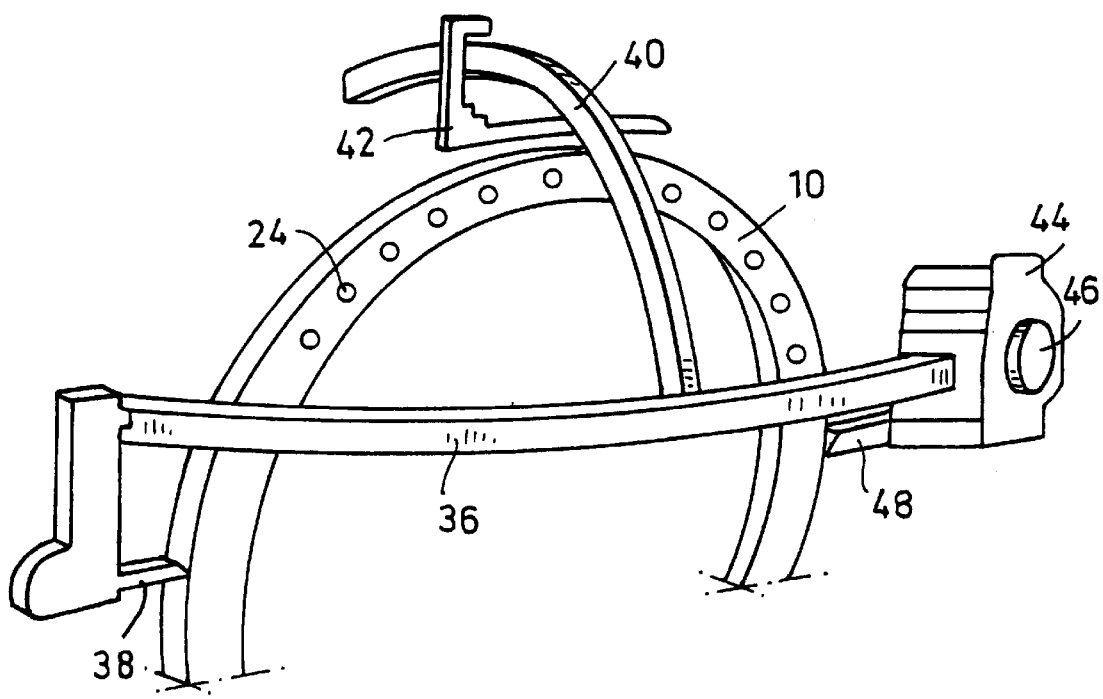
FIG. 5 is a perspective view of an arch provided with an auxiliary arch.

The whole body stereotaxis apparatus according to FIGS. 1 and 2 comprises a base plate 2 which is formed of layers of carbon fibers and acrylic foam which are superposed in sandwich-like fashion. Side strips 4 and 6 are fixed to the margins or side edges of the base plate 2, which laterally delimit the base plate and serve for holding superstructures and accessories, respectively. The side strips are made of a material the same as that of the base plate. They have lateral bores 18 which serve for connecting superstructures. A central strip 8 is fixed to the base plate in the longitudinal direction and approximately in the middle thereof. This central strip has blind bores 22 for receiving accessories. A plurality of blind bores 22 are fixed to and distributed along the central strip 8.

An arch 10 extending over the base plate 2 is secured to the two side strips 4 and 6. In its position of mounting, this arch has two vertical sections and a curved section which connects the two vertical sections and in which mounting bores 24 are formed. The arch 10 is fixed to the side strip 4 by a mounting member 14. The arch 10 has a corresponding mounting member for fixation to the side strip 6.

An arch 12 corresponding to the arch 10 is fixed to the side strips 4 and 6 behind the arch 10 at a certain distance such that it extends essentially parallel to the arch 10. The arch 12 is fixed to the side strip 4 by a mounting member 16 and to the side strip 6 by a corresponding mounting member (not shown). Mounting bores 24' corresponding to the mounting bores 24 are formed in the curved section of the arch 12. A holding bar 26 is accommodated in opposite mounting bores 24 and 24' of the two adjacent arches 10 and 12. It serves for holding accessories, particularly surgical instruments. However, it is also possible to fasten to the mounting bores calibration means for calibrating the stereotaxis apparatus as well as target setting means for the subsequent irradiation of the patient.

Three calibration members arranged one behind the other are fixed in the form of localization plates 20 to the central strip 8 in the embodiment shown in FIG. 1. The localization plates 20 have a triangular shape in cross-section and are received in one of the bores 22 of the central strip 8 by a journal or pin formed on the bottom side of the triangular tip. FIG. 2 shows the embodiment of FIG. 1 in a lateral perspective view from the left.

FIG. 3 shows the design and shape of an arch 10 and 12, respectively, of the invention. The arch has a section extending in a straight line and perpendicularly, in a projection of which two opposite bores 28 are formed for fixing a localization plate 20 or target setting means. A curved section borders on this section, in which the mounting bores 24 mentioned above already are formed for inserting holding bars 26. Finally, an end portion borders on the curved section, in which mounting bores 30 are formed again for a localization plate 20 or target setting means. The vertical dashed center line shows a possible partition line of the arch which is developed in two parts. The two-part arch can be used either as one part or initially be mounted as two parts, one part then being adapted to be disassembled.

FIG. 4 shows the shape of a holding metal sheet 32 which can be arranged between side strip 4, 6 and immobilizing means for the patient, particularly a vacuum mattress. The holding metal sheet 32 is preferably curved and has two slots 34 serving for increasing the flexibility.

FIG. 5 shows an arch 10 which is provided with an additional transversely supported auxiliary arch 36, e.g. for applications in biopsy. The auxiliary arch 36 is fixed to the arch 10 by two punctual immobilizing means 38, 48 and has a slide 44 which is slidably supported along its length and can be detached or fixed by a knurled nut 46. Various surgical instruments, particularly for biopsy, can be secured to the slide 44. The transverse arch 36 is provided with an upward arch 40 which is held in upper holding means 42 fixed to the arch 10. When the holding means 42 is detached, the transverse arch 36 can be adjusted and fixed again by sliding the upward arch 40 as regards its height with respect to the arch. Thus, the transverse arch 36 permits the attachment of a plurality of further surgical instruments in addition to the holding bar.

We claim:

1. A whole body stereotaxis apparatus, comprising:
   a base plate to accommodate a patient,
   two side strips secured to said base plate at respective marginal or side edges thereof, laterally delimit said base plate a first arch secured to the side strips;
   a second arch secured to the side strips; and
   at least one holding bar connecting said first and second arches, adapted to hold surgical instruments.

2. A whole body stereotaxis apparatus according to claim 1, further comprising a central strip secured to said base plate and having bores therein to receive accessories.

3. A whole body stereotaxis apparatus according to claim 1, further comprising calibration means providing a defined reference point in computer tomography, secured to at least one of said central strip and arches.

4. A whole body stereotaxis apparatus according to claim 3, wherein said calibration means comprises a localization plate that is substantially triangular in cross-section and adapted to receive metal wires.

5. A whole body stereotaxis apparatus according to claim 1, further comprising target setting means for subsequent irradiation of the patient, coupled to at least one of said arches.

6. A whole body stereotaxis apparatus according to claim 1, wherein said base plate is formed of a material comprising carbon fibers.

7. A whole body stereotaxis apparatus according to claim 1, wherein said base plate is formed of a material comprising acrylic foam.

8. A whole body stereotaxis apparatus according to claim 1, wherein said base plate comprises a multilayer construction including alternating layers of acrylic foam and carbon fibers.

9. A whole body stereotaxis apparatus according to claim 1, further comprising immobilizing means for the patient, on said base plate.

10. A whole body stereotaxis apparatus according to claim 9, further comprising holding metal sheets disposed between one of said side strips and the immobilizing means.

11. A whole body stereotaxis apparatus according to claim 10, further comprising a first localization plate fixed to one of said arches and a second localization plate to the central strip, wherein said first and second localization plates are in vertical alignment with each other.

12. A whole body stereotaxis apparatus according to claim 9, wherein the immobilizing means comprise a vacuum mattress.

13. A whole body stereotaxis apparatus according to claim 1, further comprising a surgical instrument to immobilize the spinal column of the patient, attached to said holding bar.

14. A whole body stereotaxis apparatus according to claim 1, wherein at least one of said arches comprises a disassembleable two-part assembly.

15. A whole body stereotaxis apparatus according to claim 1, further comprising three cooperating target setting means attached to one of said first and second arches.

16. A whole body stereotaxis apparatus according to claim 1, further comprising an auxiliary arch secured to one of said first and second arches.

17. A whole body stereotaxis apparatus according to claim 16, further comprising a slide slidably mounted on said auxiliary arch.

\* \* \* \* \*

UNITED STATES PATENT AND TRADEMARK OFFICE
CERTIFICATE OF CORRECTION

PATENT NO : 6,045,558

DATED : April 4, 2000

INVENTOR(S) : Otto Pastyr and Wolfgang Schlegel

It is certified that error appears in the above-identified patent and that said Letters Patent is hereby corrected as shown below:

| | |
|---|---|
| Column 4, line 8: | after "thereof," insert -- to -- |
| Column 4, line 9: | after "base plate" insert -- ; -- |
| Column 4, line 9: | the word "a" should begin a new paragraph |

Signed and Sealed this

Twenty-seventh Day of March, 2001

*Attest:*

NICHOLAS P. GODICI

*Attesting Officer*

*Acting Director of the United States Patent and Trademark Office*